United States Patent [19]

Javitt

[11] Patent Number: 5,376,652
[45] Date of Patent: Dec. 27, 1994

[54] ADMINISTRATION OF A 27-HYDROXYCHOLESTEROL OR RELATED COMPOUND OR STEROL-27-HYDROXYLASE STIMULANT TO PREVENT RESTENOSIS FOLLOWING VASCULAR ENDOTHELIAL INJURY

[75] Inventor: Norman B. Javitt, New York, N.Y.

[73] Assignee: New York University Medical Center, New York, N.Y.

[21] Appl. No.: 159,226

[22] Filed: Nov. 30, 1993

[51] Int. Cl.$^5$ .......................................... A61K 31/575
[52] U.S. Cl. .................................. 514/177; 514/178; 514/181; 514/182
[58] Field of Search ............... 514/182, 177, 178, 181, 514/58

[56] References Cited

U.S. PATENT DOCUMENTS 4,427,688 1/1984 Javitt .
4,939,134 7/1990 Javitt et al. .

OTHER PUBLICATIONS

Zhou, et al., Proc. Soc. Exp. Biol. Exp. Biol. Med., 202:75–80 (1993).
Nassem, et al., Biochem. Internat., 14:71–84 (1987).
Baranowski, et al., Atherosclerosis, 41:255–260 (1982).
Kandutsch, et al., Science, 201, 498 (1978).
DeCaprio, et al., Journal of Lipid Research, vol. 33, pp. 441–443 (1992).

Primary Examiner—Johann Richter
Assistant Examiner—Michael B. Hydorn
Attorney, Agent, or Firm—Sughrue, Mion, Zinn, Macpeak & Seas

[57] ABSTRACT

A method for preventing or reducing restenosis wherein a 27-hydroxycholesterol or a 25,26 and/or 27-aminocholesterol, or a sterol 27-hydroxylase stimulant is administered in a restenosis preventing and/or reducing amount.

24 Claims, No Drawings

ADMINISTRATION OF A 27-HYDROXYCHOLESTEROL OR RELATED COMPOUND OR STEROL-27-HYDROXYLASE STIMULANT TO PREVENT RESTENOSIS FOLLOWING VASCULAR ENDOTHELIAL INJURY

BACKGROUND OF THE INVENTION

Various surgical bypass and angiographic procedures are routinely employed for increasing blood flow to an organ, usually the heart. These operative and non-operative procedures injure to a greater or lesser extent the interior wall of the lumen of the blood vessel at the target site. This endothelial injury often leads through a cascade of events to restenosis. For example, balloon, laser or rotameter angioplasty, in which a catheter is inserted into the arterial system to place a balloon, laser or blade at the stenosis, is quite successful in widening a narrowed area of a blood vessel lumen. However, endothelial injury occurs at the site of the lesion, leading to restenosis in an estimated 20–40% of patients.

It has been shown in animals that endothelial injury initiates a process that leads to narrowing of the injured artery (stenosis), and this model is related and is used to study the events that occur following endothelial injury.

The major current theory for explaining restenosis is that once the endothelial cells are injured or removed by the invasive procedure, circulating platelets cover the denuded areas and release potent growth factors, such as platelet derived growth factor, which stimulate the growth and migration of underlying smooth muscle cells. Other growth factors such as fibroblast growth factors have also been implicated. For these reasons, anti-growth factors are being evaluated for the prevention of atherosclerosis.

Many factors are thought to potentially participate in restenosis. Further, hemodynamic forces responsible for the original lesion are not generally alleviated by angioplasty and may be aggravated at plaque disruption. The thrombo-resistant nature of the arterial lumen is reduced due to the generation of markedly thrombogenic surfaces of complex geometrical configuration, and changed permeability characteristics permitting possible direct interaction between blood-borne elements such as the aforementioned platelets and the arterial lumen. In summary, the surgical and angiographic procedures necessarily result in injury to vessel walls, which results in restenosis in 20–40% of patients.

27-hydroxycholesterol (cholest-5-ene-3$\beta$,27-diol) is normally present in biological fluid after neonatal life. Recently, the IUB changed certain rules of nomenclature, and the compound now referred to as 27-hydroxycholesterol was previously called 26-hydroxycholesterol. Two methyl groups are attached to carbon number 25 of cholesterol, but only one can be enzymatically hydroxylated, which was previously named carbon number 26, but is now named as carbon number 27.

U.S. Pat. No. 4,427,688 by Javitt describes the administration of 26-hydroxycholesterol (sic., 27-hydroxycholesterol) and various derivatives and analogs thereof for reducing cholesterol synthesis and/or cholesterol accumulation in the body tissues; hence, teaching the use of 27-hydroxycholesterol compounds for the treatment of atherosclerosis. Thereafter, as disclosed in U.S. Pat. No. 4,939,134, Javitt, et al. discovered that 27-aminocholesterol and certain amino-substituted analogs and derivatives thereof, are more potent inhibitors of cholesterol synthesis and accumulation than 27-hydroxycholesterol.

Javitt filed Japanese application 107488/82 in 1982, published as 019206/91 on Nov. 14, 1991 ("JPA"), largely corresponding in disclosure to U.S. Pat. No. 4,427,688 with insertion of additional information for further supporting use of 27-hydroxycholesterol in treatment of atherosclerosis. The JPA notes that Kandutsch, et al., *Science,* 201, 498 (1978) mentioned that oxygenated cholesterol has an inhibitory effect on the proliferation of fibroblasts and lymphocytes in vitro, perhaps by inhibiting HMG CO-A reductase, the rate-limiting enzyme in cholesterol biosynthesis, which is consistent with the idea that cholesterol is essential to cell proliferation. Javitt tested this theory by seeding hamster aortic smooth muscle cells at low density in culture wells and coulter counting control and 27-hydroxycholesterol exposed cells six days later. The 27-hydroxycholesterol at the tested concentration inhibited the proliferation by about 50%. Although a potential lead, in vitro muscle cell proliferation inhibition, in itself, does not teach nor suggest the use of the same substance for preventing restenosis in vivo. Indeed, some have interpreted the inhibitory effect by oxysterols on vascular smooth muscle cells as a toxic effect. Zhou, et al., *Proc. Soc. Exp. Biol. Med.,* 202:75–80; Nassem, et al., *Biochem. Internat.,* 14:71–84. Also see Baranowski, et al., *Atherosclerosis,* 41:255–260. Further, it has been recently reported that high doses of Lovastatin, a potent cholesterol lowering drug, in a randomized, double blind placebo controlled trial, did not decrease restenosis six months following percutaneous transluminal coronary angioplasty, although the Lovastatin did markedly decrease LDL-cholesterol level, as expected. Thus, as of today, the cholesterol lowering biological activity of a drug, while perhaps indicating potential use in the treatment of atherosclerosis, is not predicative nor suggestive of use for combating restenosis. As discussed above, restenosis is a multifaceted phenomena, distinct from atherosclerosis, and the mechanism of which is at best only partially understood.

SUMMARY OF THE INVENTION

Hereinafter, the currently accepted nomenclature for the sterol nucleus involved herein, 27-hydroxycholesterol, is employed. It is understood that this compound is identical to the compound named 26-hydroxycholesterol in the prior art discussed above as well as other prior art.

It has now been found that 27-hydroxycholesterol effectively reduces restenosis following injury to the blood vessel lumen which occurs when the lumen is widened by catheter procedure. Therefore, it is an object of the present invention to provide a method for reducing the instance of restenosis which occurs following surgical by-pass procedures and percutaneous angiographic procedures. Further, it is expected that related compounds such as 25-, 26-, and/or 27-aminocholesterol will have a similar effect on the blood vessel lumen.

Another object of the present invention is to provide a method for reducing the occurrence of restenosis after balloon, laser or rotameter angioplasty. A further aspect of the present invention involves the administration of a 27-hydroxycholesterol or related compound immediately following injury to the lumen of a blood vessel as a result of a mechanically widening thereof, and to continue to administer said compound to a patient in a maintenance dosage to prevent restenosis.

In still another embodiment of this invention, the 27-hydroxycholesterol or related compound is administered orally or intravenously, preferably intravenously dissolved in an aqueous solution of a β-cyclodextrin such as 2-hydroxypropyl-β-cyclodextrin.

In another embodiment of the present invention, a sterol 27-hydroxylase stimulant is administered to thereby increase the synthesis of 27-hydroxycholesterol in the vascular tissue, this aspect of the invention based on a finding of sterol 27-hydroxylase activity in aortic endothelial cells.

Other objects of the invention will be apparent to the skilled artisan from the detailed description of the invention hereinbelow.

DETAILED DESCRIPTION OF THE INVENTION

The compounds for use in the practice of the present invention are, in general, known in the art, and may be represented by the following formula:

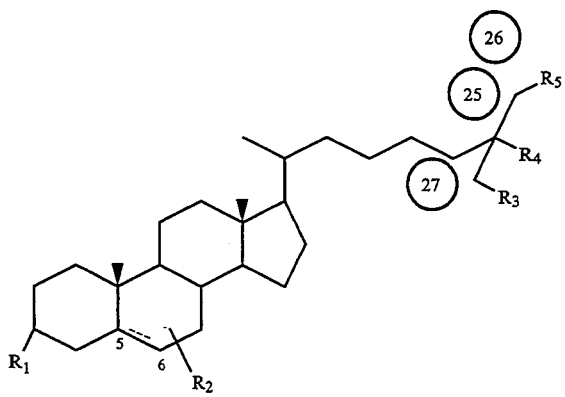

I wherein $R_1$ is hydroxyl or keto; $R_2$ is hydrogen, hydroxyl or keto; $R_3$ is hydroxyl, hydrogen or amino; $R_4$ and $R_5$ are hydrogen or amino; with the provisos that when $R_3$ is hydroxyl both $R_4$ and $R_5$ are hydrogen and when $R_3$ is not hydroxyl, at least one of $R_3$, $R_4$ and $R_5$ is amino (—$NH_2$) and the other(s) of them are hydrogen or amino, and pharmaceutically acceptable derivatives and salts thereof. In formula (I), $R_3$ is substituted at position 27.

A preferred group of compounds for use in the practice of the present invention are those within formula (I) wherein the 27-position ($R_3$) is substituted by hydroxyl or amino and each of $R_4$ and $R_5$ is hydrogen.

At this time, the most preferred compound for use in the inventive process for reducing and/or preventing restenosis is 27-hydroxycholesterol.

Other compounds usable herein include 25-aminocholesterol, 26-aminocholesterol, 27-aminocholesterol, 27-nor-25-amino-cholesterol, 25-amino-cholesta-4,6-dien-3-one, 25-amino-cholest-4-en-3-one, 22-aminocholest-5-en-3,B-ol, 20-amino-25,26,27-trinorcholest-5-ene-3,B-ol, 25-amino-cholesta-3,5-dien-7-one.

For administration to a patient, the compounds of the present invention can be provided, per se, or as the mono and diesterified derivatives and other pharmaceutically acceptable derivatives thereof such as the mono- and diethers. Most usually, fatty acid, the same or analogous to those naturally occurring, would be used to form the esters, but other inorganic and organic esters, such as acetates, the sulfates, carbonates and glucuronides, routinely employed in preparing pharmaceutically acceptable esters could be used. Esterification and/or etherification can occur at the 3- and/or 27-position, or at carbon positions 6 or 7 when $R_2$ is hydroxyl. Aryl and/or alkyl ethers, such as methyl, ethyl or cycloalkyls (i.e., cyclopentyl ethers) are contemplated. Furthermore, acid salts and various substituted compounds, for example, those containing elements such as fluorine commonly used in modification of steroid-type compounds, as long as pharmaceutically acceptable, can be used.

Administration can be through the use of liquid and solid formulations and also through the use of injectables, such as intravenous injectables, wherein conventional pharmaceutical carriers would be employed.

Suitable pharmaceutical preparations include tables, capsules, oral liquids and parenteral injectables. Tablet and capsule formulations can be employed utilizing conventional diluents, excipients and the like such as lactose in conventional capsule and tablet-making procedures. Parenteral injections could employ solvents conventionally used with lipid-soluble materials, or a salt of the sterol could be prepared, at least some of which should be soluble in aqueous solvents.

It has been difficult to form aqueous solutions of the compounds found herein for parenteral administration. None of the vehicles commonly used to solubilize steroids and bile acids, such as propylene glycol, ethanol, dimethyl sulfoxide or dimethyl formamide, is able to maintain solubility when diluted with aqueous media. As disclosed by DeCaprio, Yen and Javitt, *Journal of Lipid Research*, Vol. 33, pp. 441–443, 1992, 27-hydroxycholesterol and it is expected the related compounds involved herein, can be stabilized in aqueous media by inclusion of a cyclodextrin therein. It has been theorized that the cyclic structure of the cyclodextrin provides a lipophilic interior in which compounds that have limited aqueous solubility will form a soluble complex. The β-cyclodextrins usable for this purpose are known in the art and are inclusive of the 2-hydroxypropyl-β-cyclodextrin described by DeCaprio, et al., supra. Other non-toxic cyclodextrins would be usable.

The compounds of the present invention are administered in amounts ranging from 10 mg/kg to 100 mg/kg, preferably about 20 mg/kg to 40 mg/kg, 1 to 3 times a day.

In one embodiment of the present invention, the compound of the present invention is administered as a bolus, employing a dosage toward the upper end of the above dosage range, immediately prior to, during and/or following the blood vessel lumen widening, followed by reduction to a maintenance dosage toward the lower end of the above dosage range. It is contemplated that the maintenance dosage would continue over a prolonged period of time of, for example, 1 to 5 months.

The following example is provided to illustrate the above-described aspect of the present invention:

EXAMPLE 1

Valcular Injury Model

New Zealand white rabbits weighing 2.6 to 5.1 kgs were anesthetized with intramuscular ketamine 35 mg/kg. Additional injections of ketamine (100 mg/cc)

and xylazine (20 mg/cc) in a 50/50 mixture were given as necessary in 1 ml increments. Keflin (Eli Lilly & co.), 30/mg/kg was given intravenously (IV). A longitudinal incision was made on the medial aspect of the distal hind limb to expose the greater saphenous artery. Arteriotomy was performed, and a 3-F Fogarty embolectomy catheter (Edwards laboratories, Santa Ana, Calif.) was introduced and advanced to the level of the diaphragmatic abdominal aorta. The catheter was withdrawn from the abdominal aorta with the balloon inflated to a pressure of about 20 mmhg. This maneuver was repeated for a total of three passes. The catheter was removed, and the saphenous artery was ligated. The wound was irrigated and closed with 4-0 Dexon suture.

Specimen Analysis

The abdominal aortas were fixed by perfusion with glutaraldehyde at physiological pressure via a catheter (14G Intracath) placed in the left ventricle. One micron longitudinal sections of epoxy embedded aorta specimens were cut, stained, and computer imaged. The entire intimal and medial areas in more than 2 sections per specimen were measured using Lucida computer calculation (Micro Brightfield, Inc.). The degree of intimal thickening was determined by calculating the intimal to medial area (I/M) ratio. Statistical significance of the difference in intimal/medial ratio between groups was calculated using student t-test.

Run I

Using the above procedure, a study was carried out employing five control balloon injury rabbits and two groups, each of five balloon injury test rabbits, for receiving 27-hydroxycholesterol or suramin, the latter having been shown to inhibit intimal proliferation.

On the day before surgery, 10 mg 27-hydroxycholesterol dissolved in 1.0 ml of 45% aqueous solution of 2-hydroxypropyl-$\beta$-cyclodextrin (HPBCD) was administered intravenously to one group of five test rabbits. Suramin was administered to the other test group. bFGF was administered throughout the testing period.

On the day of surgery, a short time prior to the balloon angioplasty, the five test rabbits were administered another 5 mg of 27-hydroxycholesterol in 0. 5 ml HPBCD, and the same dosage was administered to each of the five test rabbits twice a day on days 1 to 14 following the day of balloon angioplasty, in the form of 5 mg 27-hydroxycholesterol in 0.5 ml 45% HPBCD twice a day. On day 14, the above specimen analysis was carried out on the fifteen rabbits, with the following results.

| QUANTITATIVE HISTOLOGICAL EVALUATION OF ARTERIAL WALL 14 DAYS | | |
|---|---|---|
| | Mean Intima/Media Ratio[1] | |
| | 5-DAY | 14-DAY |
| Control (28 rabbits) | 0.094 ± 0.006 | 0.5542 ± 0.024 |
| Suramin Administration | | 0.4089 ± 0.034[2] |
| 27-OHcholesterol Administration | | 0.4872 ± 0.0238 |

[1]Ratio of thicknesses of intima and media of artery wall
[2]$p < 0.05$

This run suggests an improved intima/media ratio through the administration of 27-hydroxycholesterol. However, the results were not as good as with suramin and when calculated, the difference between the control group and the 27-hydroxycholesterol group was not statistically significant. With a suggestion of utility, a further run was carried out with increased Run II 27-hydroxycholesterol dosage.

Control (vehicle alone) and 27-hydroxycholesterol test rabbits were used as in Run I, with the exception that each test rabbit received 100 mg 27-hydroxycholesterol dissolved in 5.0 ml 45% HPBCD subcutaneously on the day before surgery, the day of surgery and on days 1 to 14 following surgery.

| QUANTITATIVE HISTOLOGICAL EVALUATION OF ARTERIAL WALL 14 DAYS | |
|---|---|
| | Mean Intima/Media Ratio |
| Control (28 rabbits) | 0.5209 [±.001?] |
| Test (20 rabbits) | 0.2880 [±.024?] |

The 27-hydroxycholesterol reduced degree of intimal thickening by nearly ½ as compared with the control group.

In a second aspect of the present invention, a sterol-27-hydroxylase stimulant is administered to increase the sterol-27-hydroxylase activity present in vascular tissue, the presence thereof in vascular tissue being heretofore unknown. In this manner not only is the available amount of 27-hydroxycholesterol enhanced since it is one of the major metabolites from sterol-27-hydroxylase activity, but the 27-hydroxycholesterol is produced in the cells at the location where it is best utilized by the body in reducing and/or preventing restenosis.

The sterol 27-hydroxylase activity in bovine aortic endothelial (BAE) cells in culture has been compared with that in Hep G2 cells and in chinese hamster ovary (CHO) cells using identical culture conditions. The total enzyme activity of BAE cells (3.0 nmol/72 h/mg cell protein) was comparable with that of Hep G2 cells (4.0 nmol/72 h/mg protein) and both values were significantly greater than that in CHO cells (0.002 nmol/72 h/mg protein). The enzyme was identified in BAE cells by Western blotting using an antibody of proven specificity, and its metabolites 27-hydroxycholesterol and 3$\beta$-hydroxy-5-cholestenoic acid were identified by mass spectrum analysis. The presence of the enzyme in endothelium provides a mechanism for providing the biologic effects of 27-hydroxycholesterol in vascular tissue.

EXAMPLE 2

Cell Culture

Bovine aortic endothelial (BAE) cells obtained from a slaughterhouse were plated at low density ($2 \times 10^5$ cells/cm$^2$) in 100-mm dishes and were grown to confluence in Dulbecco's modified Eagle medium (DMEM) supplemented with 10% fetal bovine serum (FBS), 50 units/ml penicillin, and 50 units/ml streptomycin at 37° C. in a 5% $CO_2$ atmosphere. The confluent monolayer was rinsed once with Hank's balanced salt solution, and 4 ml of DMEM containing 10% delipidated FBS and either 20 $\mu$M cholesterol dissolved in 2-hydroxypropyl-$\beta$-cyclodextrin or an equivalent amount of vehicle alone was added to each dish. Hep G2 cells and chinese hamster ovary cells (CHO) were cultured under identical conditions and for the same length of time. At 24-h intervals the media and cells were harvested. The medium obtained from each dish was analyzed for metabolites. Cells were pooled for immunoblot analysis.

Western Blotting

Samples were subjected to electrophoresis on a 10% SDS-polyacrylamide gel and were transferred onto a nitrocellulose membrane by an electrophoretic technique. Antibody was raised in rabbits against residues 15 to 28 of the 27-hydroxylase protein. Visualization was accomplished using an alkaline phosphatase-conjugated goat and anti-rabbit antibody followed by the Rad-free kit for colorimetric detection of Western blots (Schleicher & Schuell, Keene, N.H.).

Several attempts were made to detect the 56-kb 27-hydroxylase protein in mitochondria prepared from BAE cells, but despite the use of protease inhibitors the predominant immunoreactive band was detected at 35 kd, with occasionally a faint band at 56 kd. Boiling freshly harvested whole cells in loading buffer appears to have prevented proteolysis.

GLC-MS Analysis

Sample Preparation

To 1 ml of harvested medium, internal standards (500 ng each) of deuterated 27-hydroxycholesterol, $3\beta$-hydroxy-5-cholestenoic acid (prepared by Jones oxidation of the 3-monoacetate of the deuterated 27-hydroxysterol), and $^{13}C$-$3\beta$-hydroxy-5-cholenoic acid were added and allowed to equilibrate for 30 min at room temperature. Following acidification and extraction into ethyl acetate, the dried residue was saponified. In some studies solvolysis was also done prior to extraction. The dried extract was applied to a Silica gel G TLC plate together with authentic standards in parallel lanes; after development (chloroform/acetone, 97:3) the standards were visualized by spraying with phosphomolybdic acid and the appropriate areas of the plate were removed for elution of 27-hydroxy-cholesterol and the $C_{27}$ and $C_{24}$ acids. The diacetate of 27-hydroxycholesterol and methyl acetates of the $C_{27}$ and $C_{24}$ acids were then prepared using dimethoxy-propane/HCl for methylation and pyridine/acetic anhydride for acetylation. It was found that complete methylation of the $C_{27}$ acid with dimethoxypropane/HCl took longer than that of the $C_{24}$ acid. Therefore methylation was allowed to proceed at room temperature overnight (approximately 18 h). Formation of a 3-methoxy derivative by this prolonged methylation procedure was not detected.

Isotope Ratio Mass Spectrometry

Using a Hewlett-Packard GLC-MS (Model #5890-5970) and a fused silica column (CP-sil 19 CB, 0.25 mm i.d., 25 m length; Chrompack, Raritan, N.J.), the appropriate TLC fractions were injected in the splitless mode with temperature programming from 260° C. to 270° C. at 1.0° C./min and a column head pressure of 5 psi.

To quantify 27-hydroxycholesterol the detector was programmed in the simultaneous ion monitoring mode for m/z 426 [mol ion diacetate=486–60 (acetate)]and m/z 430, and the amount of endogenous 27-hydroxycholesterol was calculated from the respective areas. For the $C_{27}$ acid the ion pair that was used was m/z 412 [methyl ester acetate mol ion=476–60 (acetate)]and m/z 416, and for the $C_{24}$ acid m/z 370 [mol ion methyl ester acetate=430–60 (acetate)]and m/z 373.

Results

Both the spectra and the retention times of 27-hydroxycholesterol and of $3\beta$-hydroxy-5-cholestenoic acid isolated from the sterol-free medium that was in contact with BAE cells for 72 h are identical to authentic standards of the diacetate and methyl ester diacetate derivatives, respectively.

After the identity of these compounds was established by complete spectrum analysis, an isotope ratio program was used to compare their rates of synthesis in sterol-free and cholesterol-supplemented medium. As shown in Table 1, medium containing 20 nmol/ml of cholesterol yielded a much greater amount of metabolites than sterol-free medium. At 72 h the metabolites represented approximately 5.8% of the cholesterol added to the medium [(1.029+0.211)−(0.103+0.079)×100÷20]. Although the amount of 27-hydroxycholesterol in the medium was relatively constant from 24 to 72 h, a progressive increase in the amount of $3\beta$-hydroxy-5-cholestenoic acid occurred. For BAE cells maintained in nonsupplemented medium the proportion of $C_{27}$ acid rose from 12% at 24 h to 43% at 72 h. In contrast, although the absolute amount of the $C_{27}$ bile acid that was synthesized was greater in cholesterol-supplemented medium, it represented only 3.8% of total metabolite at 24 h and increased to 17% at 72 h.

The activity of sterol 27-hydroxylase in BAE cells was compared with that in Hep G2 and CHO cells using the cholesterol-supplemented medium. As shown in Table 2, the amount of 27-hydroxycholesterol in the medium collected from BAE cells at 72 h was greater than that from Hep G2 cells. The amount present in medium from CHO cells was below our limit of detection (10 ng per assay).

The medium from CHO cells always contained a small amount of $3\beta$-hydroxy-5-cholenoic acid, which was much less than that found in the medium from Hep G2 or BAE cells.

Because Hep G2 cells synthesize $3\beta$-hydroxy-5-cholenoic acid from 27-hydroxycholesterol, the medium from all the cell lines was analyzed for this derivative before and after solvolysis. No increase in the yield of $3\beta$-hydroxy-5-cholestenoic acid was obtained after solvolysis of media derived from Hep G2 or the other cell lines. Medium from Hep G2 cells was found to contain $3\beta$-hydroxy-5-cholenoic acid, which increased in amount following solvolysis.

Since all the metabolic products are derived from the sterol 27-hydroxylase activity of the cells, the total amounts produced by Hep G2 and BAE cells are comparable and are much greater than that from CHO cells.

TABLE 1

Synthesis of 27-hydroxycholesterol and
$3\beta$-hydroxy-5-cholestenoic acid by BAE Cells: Time course and
effect of cholesterol added to the medium

| Culture Medium | 24 h | 48 h | 72 h |
|---|---|---|---|
| 27-hydroxycholesterol (pmol/ml medium) | | | |
| Delipidated FBS[a] (n = 4)[b] | 89 ± 12[c] | 98 ± 11 | 103 ± 9 |
| +20 nmol/ml cholesterol | 1089 ± 111 | 1064 ± 161 | 1029 ± 99 |
| $3\beta$-hydroxy-5-cholestenoic acid (pmol/ml medium) | | | |
| Delipidated FBS | 11.9 ± 1.3 | 32.0 ± 1.9 | 78.6 ± 11 |
| +20 nmol/ml choles- | 42.5 ± 6.1 | 112 ± 12.4 | 211 ± 48.3 |

TABLE 1-continued

Synthesis of 27-hydroxycholesterol and
3β-hydroxy-5-cholestenoic acid by BAE Cells: Time course and effect of cholesterol added to the medium

| Culture Medium | 24 h | 48 h | 72 h |
|---|---|---|---|
| terol | | | |

[a] Delipidated fetal bovine serum
[b] Number of dishes
[c] Mean ± standard deviation

TABLE 2

Comparison of Sterol 27-hydroxylase activity in BAE, Hep G2 and CHO cells

| Cells[a] | Metabolites Derived from Sterol 27-Hydroxylase (pmol/mg/cell protein) | | | |
|---|---|---|---|---|
| | 27OH-chol.[b] | 3βOH-5-cholest. a. | 3βOH-5-cholen. a. | Total |
| BAE (n = 6)[c] | 2555 ± 348 | 474 ± 118 | not detected | 3029 |
| HEP G2 (n = 6) | 1622 ± 291 | 471 ± 126 | 1940 ± 270[d] | 4033 |
| CHO (n = 3) | not detected | 2 ± 1 | not detected | 2 |

[a] All cells were maintained for 72 h in DMEM enriched with 10% delipidated FBS containing 20 μM cholesterol.
[b] 27OH-chol = 27-hydroxycholesterol; 3βOH-cholest. a. = 3β-hydroxy-5-cholestenoic acid; 3βOH-cholen. a. = 3β-hydroxy-5-cholenoic acid.
[c] Number of dishes.
[d] Mean value of 2 dishes after solvolysis.

From the above, the positive effects of this invention on restenosis can be provided by stimulating the sterol 27-hydroxylase activity of the vascular endothelium. Various stimulatory mechanisms are known, such as by the administration of steroid hormones, such as the naturally-occurring sex hormones estrogen and testosterone.

The skilled artisan will be able to select other naturally-occurring and synthetic steroid hormones for use in providing a sterol 27-hydroxylase stimulant effect.

Variations of the invention will be apparent to the skilled artisan.

What is claimed is:

1. In a process wherein in a mammal, a therapeutic procedure is carried out to reduce or remove a stenosis present within a lumen of a blood vessel, the improvement to prevent restenosis which comprises administering to the mammal a restenosis preventing amount of a compound of formula (I)

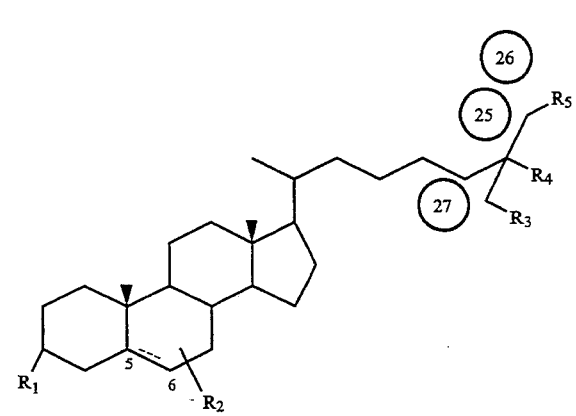

wherein $R_1$ is hydroxyl or keto; $R_2$ is hydrogen, hydroxyl or keto; $R_3$ is hydroxyl, hydrogen or amino; $R_4$ and $R_5$ are hydrogen or amino; with the provisos that when $R_3$ is hydroxyl both $R_4$ and $R_5$ are hydrogen and when $R_3$ is not hydroxyl, at least one of $R_3$, $R_4$ and $R_5$ is amino ($-NH_2$) and the other(s) of them are hydrogen or amino, and pharmaceutically acceptable derivatives and salts thereof.

2. In a process wherein in a mammal, a therapeutic procedure is carried out to reduce or remove a stenosis present within a lumen of a blood vessel, the improvement to reduce the degree of restenosis which comprises administering to the mammal a restenosis reducing amount of a compound of formula (I)

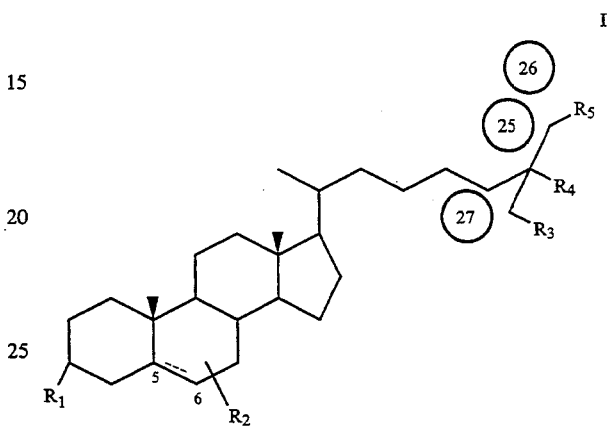

wherein $R_1$ is hydroxyl or keto; $R_2$ is hydrogen, hydroxyl or keto; $R_3$ is hydroxyl, hydrogen or amino; $R_4$ and $R_5$ are hydrogen or amino; with the provisos that when $R_3$ is hydroxyl both $R_4$ and $R_5$ are hydrogen and when $R_3$ is not hydroxyl, at least one of $R_3$, $R_4$ and $R_5$ is amino ($-NH_2$) and the other(s) of them are hydrogen or amino, and pharmaceutically acceptable derivatives and salts thereof.

3. The process of claim 1, wherein $R_3$ is hydroxyl or amino and each of $R_4$ and $R_5$ is hydrogen.

4. The process of claim 2, wherein $R_3$ is hydroxyl or amino and each of $R_4$ and $R_5$ is hydrogen.

5. The process of claim 1, wherein the compound of formula (I) administered is 27-hydroxycholesterol.

6. The process of claim 2, wherein the compound of formula (I) administered is 27-hydroxycholesterol.

7. The process of claim 1, wherein the compound of formula (I) is administered in a pharmaceutically acceptable carrier comprising an aqueous medium containing a pharmaceutically acceptable cyclodextrin in sufficient amount to stabilize the compound of formula (I) in the aqueous medium.

8. The process of claim 2, wherein the compound of formula (I) is administered in a pharmaceutically acceptable carrier comprising an aqueous medium containing a pharmaceutically acceptable cyclodextrin in sufficient amount to stabilize the compound of formula (I) in the aqueous medium.

9. The process of claim 1, wherein the therapeutic procedure is a surgical procedure.

10. The process of claim 2, wherein the therapeutic procedure is a surgical procedure.

11. The process of claim 1, wherein the therapeutic procedure is balloon, laser or rotameter angioplasty.

12. The process of claim 2, wherein the therapeutic procedure is balloon, laser or rotameter angioplasty.

13. The process of claim 1, wherein the therapeutic procedure is balloon angioplasty.

14. The process of claim 2, wherein the therapeutic procedure is balloon angioplasty.

15. The process of claim 1, wherein the compound of claim 1 is administered in an amount of about 10 to 100 mg/kg 1 to 3 times a day.

16. The process of claim 2, wherein the compound of claim 1 is administered in an amount of about 10 to 100 mg/kg 1 to 3 times a day.

17. The process of claim 1, wherein the compound of formula (I) is administered as the compound itself or as a mono- or di-ester, or mono- or di-ether thereof.

18. The process of claim 2, wherein the compound of formula (I) is administered as the compound itself or as a mono- or di-ester, or mono- or di-ether thereof.

19. The process of claim 1 wherein the compound of formula (I) is administered prior to, during and/or after the therapeutic procedure.

20. The process of claim 2 wherein the compound of formula (I) is administered prior to, during and/or after the therapeutic procedure.

21. The process of claim 1 wherein the compound of formula (I) is administered after the therapeutic procedure.

22. The process of claim 2 wherein the compound of formula (I) is administered after the therapeutic procedure.

23. In a process wherein in a mammal, a therapeutic procedure is carried out to reduce or remove a stenosis present within a lumen of a blood vessel, the improvement to reduce the degree of restenosis which comprises administering to the mammal a sterol 27-hydroxylase stimulant in an amount sufficient for reducing said degree of restenosis.

24. In a process wherein in a mammal, a therapeutic procedure is carried out to reduce or remove a stenosis present within a lumen of a blood vessel, the improvement to prevent restenosis which comprises administering to the mammal a sterol 27-hydroxylase stimulant in an amount sufficient for preventing restenosis.

* * * * *